(12) United States Patent
Beger et al.

(10) Patent No.: US 10,980,578 B2
(45) Date of Patent: *Apr. 20, 2021

(54) MEDICAL INSTRUMENTATION AND METHOD

(71) Applicant: Aesculap AG, Tuttlingen (DE)

(72) Inventors: Jens Beger, Tuttlingen (DE); Josef Kozak, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 584 days.

This patent is subject to a terminal disclaimer.

(21) Appl. No.: 15/679,418

(22) Filed: Aug. 17, 2017

(65) Prior Publication Data

US 2018/0055546 A1 Mar. 1, 2018

(30) Foreign Application Priority Data

Aug. 23, 2016 (DE) .................... 10 2016 115 605

(51) Int. Cl.
*A61B 17/70* (2006.01)
*A61F 2/44* (2006.01)
(Continued)

(52) U.S. Cl.
CPC .......... *A61B 17/7083* (2013.01); *A61B 17/84* (2013.01); *A61B 34/20* (2016.02);
(Continued)

(58) Field of Classification Search
CPC . A61B 17/7083; A61B 17/84; A61B 17/7002; A61B 17/708; A61B 34/20;
(Continued)

(56) References Cited

U.S. PATENT DOCUMENTS 6,036,691 A 3/2000 Richardson
6,226,548 B1 5/2001 Foley et al.
(Continued)

FOREIGN PATENT DOCUMENTS

DE 10045375 4/2002
DE 10314882 10/2004
(Continued)

OTHER PUBLICATIONS

IPhone5; Apple Inc. Modified: Oct. 24, 2013; URL: <web.archive.org/web/20150312201031/https://support.apple.com/kb/SP655?locale=en_US> Accessed on Internet Archive, Sep. 15, 2019. (Year 2013).
(Continued)

*Primary Examiner* — Marcela I. Shirsat
(74) *Attorney, Agent, or Firm* — Lipsitz & McAllister, LLC

(57) ABSTRACT

The invention relates to a medical instrumentation with a navigation system which comprises an optical detection unit comprising a camera, and a data processing unit coupled to the detection unit, with a medical article and with a marking device which is held directly or indirectly on the article and is positioned in a defined spatial arrangement in relation thereto, or which marking device is comprised by or formed by the article, the location and orientation of the marking device being determinable with the navigation system, it being possible for at least one image of the marking device and the article to be taken by means of the detection unit and for the position and shape of the article to be determined by the data processing unit on the basis of an image. The invention also relates to a method for determining the shape of a medical article.

18 Claims, 4 Drawing Sheets

(51) Int. Cl.
*A61B 34/20* (2016.01)
*A61B 17/84* (2006.01)
*A61B 90/50* (2016.01)
*A61B 90/00* (2016.01)
*A61B 90/30* (2016.01)

(52) U.S. Cl.
CPC .... *A61F 2/4455* (2013.01); *A61B 2034/2055* (2016.02); *A61B 2034/2057* (2016.02); *A61B 2090/309* (2016.02); *A61B 2090/372* (2016.02); *A61B 2090/3983* (2016.02); *A61B 2090/3991* (2016.02); *A61B 2090/502* (2016.02)

(58) Field of Classification Search
CPC .... A61B 2034/2057; A61B 2034/2061; A61B 2034/2065; A61B 2034/2068; A61B 90/37; A61B 2090/372; A61B 2090/3983; A61B 17/8063; A61B 2034/2055; A61F 2/4455
USPC ............... 606/102, 104; 623/17.11–17.15
See application file for complete search history.

(56) References Cited

U.S. PATENT DOCUMENTS

| | | | |
|---|---|---|---|
| 7,561,733 | B2 | 7/2009 | Vilsmeier et al. |
| 7,763,030 | B2 | 7/2010 | Blau et al. |
| 7,809,184 | B2 | 10/2010 | Neubauer et al. |
| 7,835,778 | B2 | 11/2010 | Foley et al. |
| 7,862,568 | B2 | 1/2011 | Vilsmeier et al. |
| 7,922,731 | B2 * | 4/2011 | Schumacher ........ A61B 17/708 606/104 |
| 7,957,831 | B2 | 6/2011 | Isaacs |
| 8,320,612 | B2 | 11/2012 | Knobel et al. |
| 8,534,848 | B2 | 9/2013 | Hauri et al. |
| 8,549,888 | B2 | 10/2013 | Isaacs |
| 9,314,281 | B2 | 4/2016 | Beger et al. |
| 9,414,859 | B2 | 8/2016 | Ballard et al. |
| 9,585,700 | B2 | 3/2017 | Wehrle et al. |
| 2003/0078565 | A1 | 4/2003 | Vilsmeier et al. |
| 2005/0262911 | A1 | 12/2005 | Dankowicz et al. |
| 2007/0160439 | A1 | 7/2007 | Vilsmeier et al. |
| 2009/0249851 | A1 | 10/2009 | Isaacs |
| 2010/0100081 | A1 | 4/2010 | Tuma et al. |
| 2011/0265538 | A1 | 11/2011 | Trieu et al. |
| 2011/0270262 | A1 | 11/2011 | Justis et al. |
| 2011/0286098 | A1 | 11/2011 | Hauri et al. |
| 2013/0066387 | A1 | 3/2013 | Beger et al. |
| 2013/0268007 | A1 | 10/2013 | Rezach et al. |
| 2014/0005531 | A1 | 1/2014 | Taylor |
| 2014/0225999 | A1 * | 8/2014 | Bracke .................. A61B 34/20 348/77 |
| 2014/0236159 | A1 | 8/2014 | Haider et al. |
| 2014/0311203 | A1 | 10/2014 | Crawford et al. |
| 2014/0316420 | A1 * | 10/2014 | Ballard ............. A61B 17/7002 606/102 |
| 2015/0133945 | A1 | 5/2015 | Dushyant et al. |
| 2015/0182292 | A1 | 7/2015 | Hladio et al. |
| 2015/0305786 | A1 | 10/2015 | Wehrle et al. |
| 2016/0175013 | A1 | 6/2016 | Redmond |
| 2016/0242857 | A1 | 8/2016 | Scholl |
| 2017/0000568 | A1 | 1/2017 | O'Neil et al. |
| 2017/0340367 | A1 | 11/2017 | Beger et al. |
| 2018/0049809 | A1 | 2/2018 | Marti et al. |

FOREIGN PATENT DOCUMENTS

| | | |
|---|---|---|
| DE | 102004008870 | 10/2004 |
| DE | 102005026654 | 12/2006 |
| DE | 102008022254 | 11/2009 |
| DE | 102010016448 | 10/2011 |
| DE | 202015100313 | 3/2015 |
| DE | 102014102398 | 8/2015 |
| DE | 102015102776 | 9/2016 |
| EP | 1281365 | 2/2003 |
| EP | 1413257 | 2/2005 |
| EP | 1657678 | 5/2006 |
| EP | 1719472 | 11/2006 |
| EP | 1523950 | 2/2009 |
| EP | 2910206 | 8/2015 |
| WO | 0159708 | 8/2001 |
| WO | 03020146 | 3/2003 |
| WO | 2009135838 | 11/2009 |
| WO | 2011020505 | 2/2011 |
| WO | 2013164770 | 11/2013 |
| WO | 2014088801 | 6/2014 |
| WO | 2016134911 | 9/2016 |
| WO | 2017037113 | 3/2017 |

OTHER PUBLICATIONS

Apple App Store; My Tools: My AR Ruler & Light, iDaily Corp. URL: <https://apps.apple.com/hk/app/mytools-my-ar-ruler-light/id557839389?l=en> * note earliest review for the app is dated Nov. 17, 2012. Accessed Sep. 15, 2019 (Year: 2012).

Top 10 Apps Like Mytools—My AR Ruler & Light, URL: <https://appfelstrudel.com/a/557839389/alternative-to-mytools-my-ar-ruler-light.html> "First Release Sep. 28, 2012". Accessed Sep. 15, 2019. (Year 2012).

* cited by examiner

MEDICAL INSTRUMENTATION AND METHOD

CROSS-REFERENCE TO RELATED APPLICATIONS

This application claims the benefit of German application number 10 2016 115 605.1, filed on Aug. 23, 2016 which is incorporated herein by reference in its entirety and for all purposes.

FIELD OF THE INVENTION

The invention relates to a medical instrumentation.

The invention also relates to a method for determining the shape of a medical article.

The medical article may be configured in many different ways with respect to shape and function. For example, the medical article is an implant. An example of an article in the form of an implant is a stabilization element of a medical fixation system. In a different embodiment, the medical article may be a surgical instrument.

The invention is described herein, in particular, using the example of an implant and specifically a stabilization element, but is not limited to this.

BACKGROUND OF THE INVENTION

Stabilization elements are used, in particular, as components of surgical fixation systems. For example, bones or bone fragments can be fixed relative to one another by means of such a fixation system. A typical field of application is spinal surgery during which vertebral bodies are to be secured so as to prevent movement relative to one another. Herein anchoring elements, for example, bone screws are anchored in the vertebral bodies and connected to one another by means of the stabilization element, for example, a rod. Such a fixation system is described, for example, in DE 10 2010 016 448 A1.

To perform surgery with the least possible invasiveness, it is desirable to ascertain whether the stabilization element is suitable for connecting the anchoring elements to one another so as to achieve the desired fixation. If necessary, the shape of the stabilization element can be changed or a stabilization element can be selected from a plurality of available stabilization elements of different shape. The ascertainment, the change in shape and/or the selection preferably take place prior to implantation of the stabilization element.

In patent application DE 10 2015 102 776 it is described how the shape of a stabilization element is determinable on the basis of images which are taken by means of a navigation system and are processed by a data processing unit. Devices with which the shape of surgical stabilization elements can be changed are described in DE 103 14 882 A1, US 2005/0262911 A1 and U.S. Pat. No. 8,549,888 B2.

An object underlying the present invention is to provide an instrumentation and a method with which the shape of a medical article can be determined in a simple way.

SUMMARY OF THE INVENTION

In a first aspect of the invention, a medical instrumentation is provided with a navigation system which comprises an optical detection unit comprising a camera, and a data processing unit coupled to the detection unit, with a medical article and with a marking device which is held directly or indirectly on the article and is positioned in a defined spatial arrangement in relation thereto, or which marking device is comprised by or formed by the article. The location and orientation of the marking device are determinable with the navigation system, it being possible for at least one image of the marking device and the article to be taken by means of the detection unit and for the position and shape of the article to be determined by the data processing unit on the basis of an image.

In a second aspect of the invention, a method for determining the shape of a medical article using an instrumentation in accordance with the first aspect comprises taking at least one image of the marking device and the article by means of the detection unit, and determining the position and shape of the article by the data processing unit on the basis of an image.

BRIEF DESCRIPTION OF THE DRAWINGS

The following description of preferred embodiments of the invention will serve in conjunction with the drawings to explain the invention in greater detail. Advantageous embodiments of an instrumentation in accordance with the invention are described, with which the method in accordance with the invention can be performed. There are shown in.

DETAILED DESCRIPTION

Figure 1:
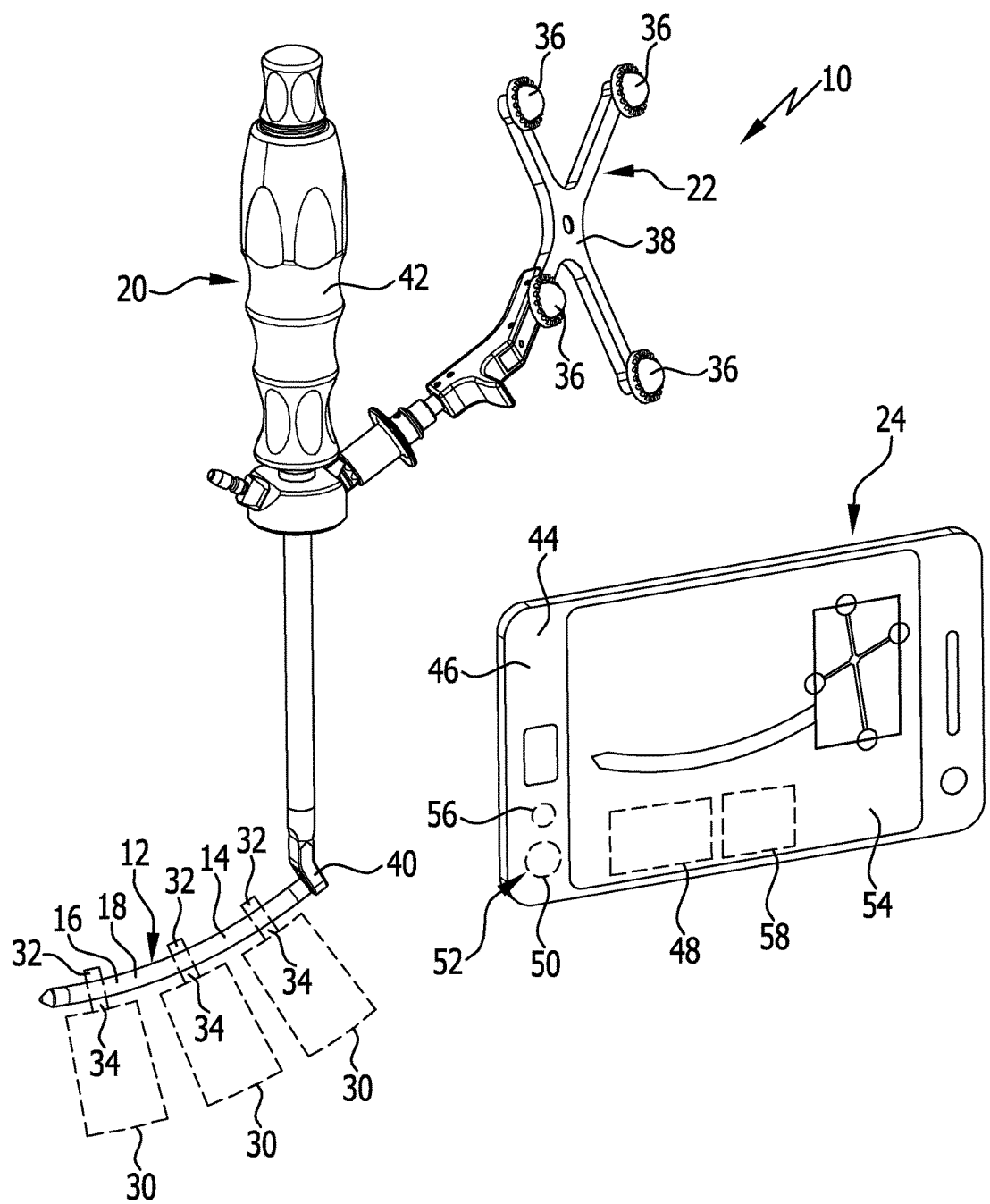
FIG. 1: a schematic perspective partial illustration of an instrumentation in accordance with the invention.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrumentation with a navigation system which comprises an optical detection unit comprising a camera, and a data processing unit coupled to the detection unit, with a medical article and with a marking device which is held directly or indirectly on the article and is positioned in a defined spatial arrangement in relation thereto, or which marking device is comprised by or formed by the article, the location and orientation of the marking device being determinable with the navigation system, it being possible for at least one image of the marking device and the article to be taken by means of the detection unit and for the position and shape of the article to be determined by the data processing unit on the basis of an image.

The present invention incorporates the concept that a marking device can be detected with respect to location and orientation and, accordingly, change in location and change in orientation by means of a medical navigation system. The location and orientation can be determined relative to the detection unit, with the marking device, for its part, defining a reference coordinate system. The navigation system comprises an optical detection unit with at least one camera with which images of the medical article, in any case, at least a section thereof, including the marking device arranged thereon can be taken. The position and the shape of the article can be determined from one image, particularly, only one image, by the data processing unit. For this purpose, image processing algorithms can be stored for execution in the data processing unit. The image processing algorithms analyze the one image of the at least one camera and using the location and/or orientation information on the basis of the marking device determine the three-dimensional shape of the article with sufficient accuracy. The determination of the position of the article can be established in the reference coordinate system owing to the defined spatial relationship of the marking device to the article.

The instrumentation in accordance with the invention allows, in particular, determination of the shape of the article without the article having to be spatially fixed for this purpose. The expenditure in terms of equipment for determining the shape of the article can thereby be kept low. This also facilitates the handling of the instrumentation.

Preferably, information about the article which is used by the data processing unit when determining the shape of the article is stored in a storage unit. For example, information about dimensions of the article, for example, its length, width or diameter can be filed in the storage unit. By comparing dimensions filed with respect to different articles in the storage unit with estimated dimensions determined on the basis of the one image, this also enables the article to be identified and the shape to be reconstructed on the basis of the information stored in the storage unit.

It may be provided that a plurality of images of the marking device and the article or at least a section thereof can be taken. These are preferably taken from a different orientation. This enables the shape of the article to be determined even more reliably.

It is expedient for more than two images of the article and of the marking device to be able to be taken in succession, on the basis of which the shape of the article is determinable, with the orientations and images differing from one another in pairs. The shape of the article can thereby be determined even more accurately.

If the article has a longitudinal extent, for example, in the configuration of a rod, the images are preferably taken with alignment of an optical axis of the at least one camera at an angle and, in particular, transversely to the longitudinal direction of the article. Between two images the camera is preferably rotated through 90° with respect to the longitudinal extent of the article.

The detection unit advantageously comprises precisely one camera in order to simplify the constructional design of the navigation system. The provision of a stereo camera is not necessary.

For a constructionally simple design and a cost-effective manufacture of the instrumentation, it is expedient for the navigation system to be a hand-held, integrated navigation system. As used herein, "integrated" is, in particular, to be understood as meaning that the detection unit and the data processing unit are arranged in a common housing. A display unit of the navigation system is preferably arranged in the housing.

For example, the hand-held, integrated navigation system is a smartphone or a tablet computer. A data processing program with which data of the detection unit can be analyzed by the data processing unit and the shape of the article determined may be stored for execution on the smartphone or tablet computer.

In an advantageous embodiment the navigation system may be or comprise smart glasses. The smart glasses may be worn in the manner of glasses or a glasses frame. It is not necessary for lenses (which may be made of glass or plastic) of the glasses to be ground or unground. A frame for resting against or on the ears and the nose, on which are held the optical detection unit with the camera, a display unit and preferably the data processing unit, is, for example, sufficient. The storage unit and/or an illumination unit may also be held on the frame. A battery for supplying energy may be provided on the smart glasses.

It is advantageous for the navigation system to comprise a display unit which is coupled to the data processing unit and on which it is possible to show or provide the images of the article and/or instructions for a user for taking the images and/or a representation of the article, determined on the basis of the images.

The navigation system may comprise an illumination unit with which light, in particular, visible light can be emitted in the direction of the marking device. The illumination unit comprises, for example, at least one LED light source and is preferably comprised by the integrated, hand-held navigation system.

The medical article may be a surgical instrument, or the medical article may be an implant.

The implant may be an implant which remains in the body or a trial implant used only temporarily, which may also be regarded as tool of the instrumentation.

The instrumentation may comprise an implantation tool for the implant, on which the implant and the marking device are held. The implantation tool is, for example, hand-guided and allows the implant to be preferably percutaneously and minimally invasively implanted. The marking device is arranged in a defined spatial arrangement in relation to the implant by way of the implantation tool. The marking device may be releasably connectable to the implantation tool. This embodiment allows the shape of the article configured as implant to be determined. At the same time, it is possible to track the implant by way of the implantation tool with the marking device held thereon during the implantation. The handling of the article is thereby significantly simplified particularly during percutaneous implantation.

The implant in an advantageous embodiment of the instrumentation is a stabilization element of a surgical fixation system. Such fixation systems and stabilization elements were already gone into at the outset.

The stabilization element may, in particular, be a rod.

The instrumentation preferably comprises a reshaping device with which the shape of the stabilization element is changeable.

The reshaping device is, for example, a bending device for bending a rod, as which the stabilization element is configured.

It is expedient for an operator to be able to be provided by the data processing unit on an indication unit of the navigation system, for example, on a display unit, with shape changing information for handling the reshaping device, in order to convert the stabilization element from the determined shape into a prescribable shape. For example, the data processing unit can compare whether the determined shape of the stabilization element corresponds to a necessary, desired shape. The necessary shape can, for example, be determined by the relative positions of anchoring elements of the fixation system being detected with the proviso that the anchoring elements are to be connected to the stabilization element. If the shape determined on the basis of the images differs from the required shape, the stabilization element can be reshaped with the reshaping device. For this purpose, the operator can be provided with shape changing information on the display unit, and the handling of the instrumentation thereby considerably simplified.

In a corresponding manner, it is expedient for shape changing information to be transferable from the navigation system via a communication interface to the reshaping device, in order to convert the stabilization element from the determined shape into a prescribable shape. The reshaping device can give the stabilization element the prescribable, necessary shape, preferably without the intervention of the operator, on the basis of the shape changing information with which it is provided.

In particular, it is conceivable for the shape of the stabilization element to be detected in situ and/or preferably changed in situ by means of the reshaping device. Alternatively, it may be provided that the shape of the stabilization element is detected ex situ and/or changed ex situ by means of the reshaping device.

As mentioned above, the article may be a surgical instrument.

In an advantageous embodiment of the instrumentation, the surgical instrument may be a screwing instrument or a drive-in instrument. With use of the marking device, the instrument may, accordingly, be a navigated screwing instrument or a navigated drive-in instrument. By means of the instrumentation, it is possible to detect any deformations of the screwing instrument (for example, an out-of-roundness) or of the drive-in instrument. The shape of the instrument, determined on the basis of the one image, can be compared with a shape of the instrument, read, for example, from a storage unit, and a deformation thereby ascertained. With use of the instrumentation, such deformations can be compensated. The user can be informed of the deformation of the instrument, for example, on a display unit of the instrumentation and adapt the handling of the instrument accordingly.

It may be provided that the article comprises or forms marking elements of the marking device, for example, the marking elements are configured as preferably reflecting points or lines on the article.

The marking device can be indirectly or directly releasably fixed or fixable on the article.

In an advantageous embodiment of the instrumentation, the marking device is connected in one piece to the article, for example, formed or welded thereon.

A predetermined breaking point is expediently provided for separating the marking device from the article. After determination of the shape of the article, the marking device can be separated from it. An article configured as implant and specifically as stabilization element can, for example, be subsequently implanted.

It may be provided that a plurality of marking devices are held directly or indirectly on the article and are positioned in a defined spatial arrangement in relation to the article or are comprised by or formed by the article, it being possible on the basis of several images which each record one marking device and a section of the article for the position and shape of the section of the article to be determined by the data processing unit. For example, a plurality of such marking devices are held on the article or formed thereby.

A respective marking device can be detected with a respective section of the article, and the position and the shape of the section of the article determined therefrom on the basis of the one image. This may preferably be carried out in situ, but ex situ detection and determination of the shape of the respective sections are also possible.

As mentioned above, the present invention also relates to a method. The object set forth at the outset is accomplished by a method in accordance with the invention for determining the shape of a medical article using an instrumentation of the aforementioned kind, wherein at least one image of the marking device and the article is taken by means of the detection unit, and the position and shape of the article are determined by the data processing unit on the basis of an image.

The advantages mentioned hereinabove in conjunction with the explanation of the instrumentation in accordance with the invention can also be achieved by performing the method. Reference is to be had in this connection to the statements made hereinabove.

Advantageous embodiments of the method in accordance with the invention result from advantageous embodiments of the instrumentation in accordance with the invention.

FIG. 1 shows a perspective illustration of an advantageous embodiment, denoted by reference numeral 10, of a medical instrumentation. The instrumentation 10 comprises a medical article 12. In the present case, the article 12 is an implant 14, namely in the form of a stabilization element 16 of a surgical fixation system. The stabilization element 16 is configured as rod 18 having a longitudinal extent.

The instrumentation 10 further comprises an implantation tool 20 for the stabilization element 16. The instrumentation 10 also comprises a medical marking device 22 and a medical navigation system 24.

Figure 2:
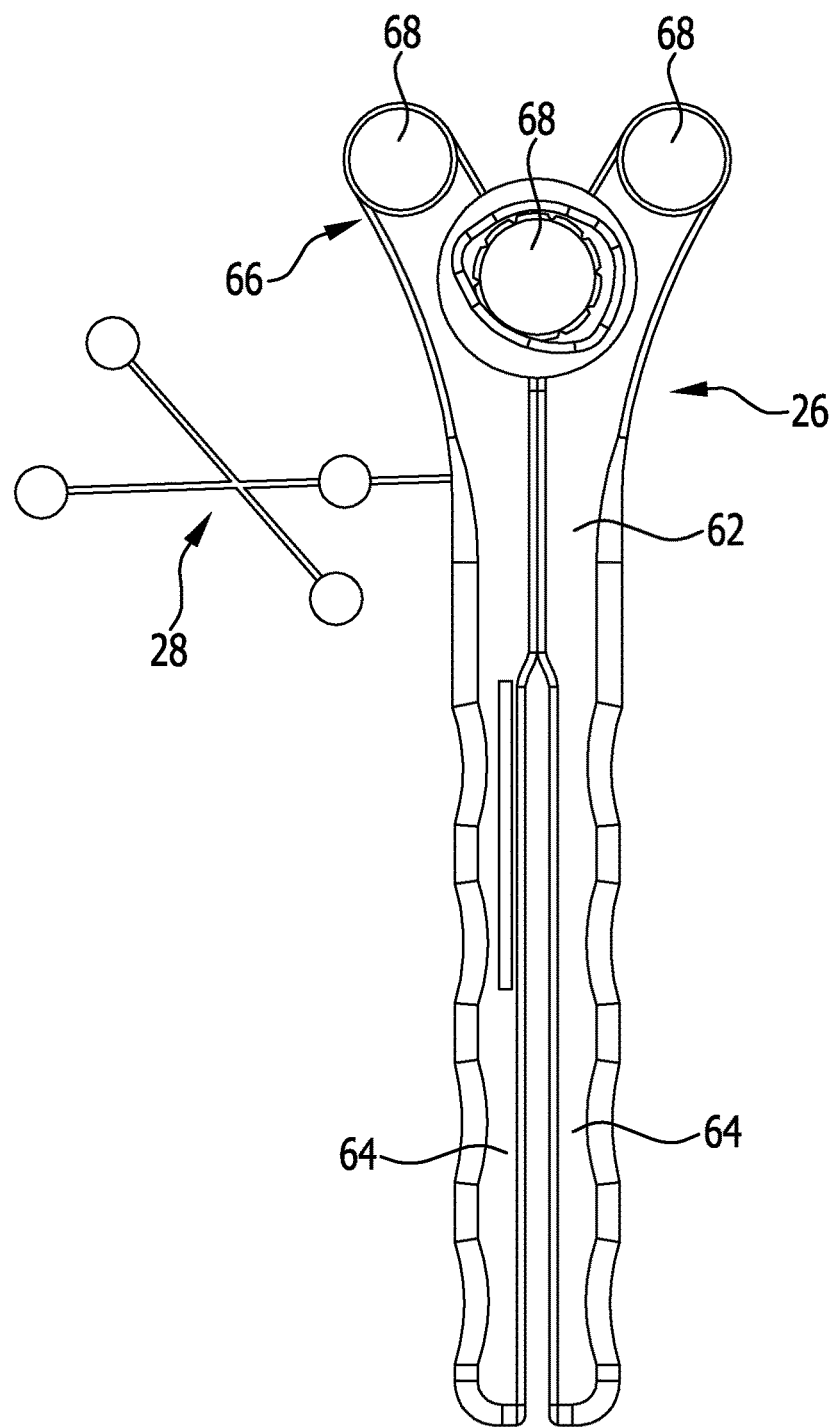
FIG. 2: a reshaping device of the instrumentation from FIG. 1.

Furthermore, the instrumentation 10 comprises a reshaping device 26 shown in a side view in FIG. 2 for reshaping the stabilization element 16 and a further medical marking device 28 arranged thereon.

The fixation system serves to fix vertebral bodies 30 shown schematically in FIG. 1 to prevent movement relative to one another. For this purpose, the fixation system has anchoring elements 32 in the form of bone screws 34, which are fixed to the vertebral bodies 30. When the fixation system is in use, the stabilization element 16 is fixed to the bone screws 34. The bone screws 34 are rigidly connectable to one another by means of the rod-shaped stabilization element 16.

To ensure the necessary relative position of the bone screws 34 and, therefore, of the vertebral bodies 30, it is important in practice for the rod 18 to have a desired, defined shape. It is also important for the position of the rod 18 to be known in view of the guidance of the implantation tool 20. The position and the shape of the rod 18 are determined, as will be explained below, by means of the navigation system 24.

In the present case, the marking device 22 is configured as so-called rigid body. The marking device 22 comprises a plurality of marking elements 36. The marking elements 36 are held on a common holder 38. The marking elements 36 are preferably of retroreflecting construction, in particular, for visible light.

In the instrumentation 10, the marking device 22 is held in a defined spatial arrangement indirectly on the rod 18. The implantation tool 20 serves this purpose. The rod 18 is, for example, held at a distal end 40 of the implantation tool 20 and assumes a defined spatial arrangement relative thereto. The marking device 22 is also held in a defined spatial arrangement on the implantation tool 20, for example, at or near a grip element 42 of the implantation tool 20.

For this reason, the spatial location and orientation of the rod 18 relative to the location and orientation of the marking device 22 are known. When the marking device 22 is tracked by means of the navigation system 24, the location and the orientation of the rod 18 can thereby also be concluded from this. The marking device 22 defines a reference coordinate system.

For easier handling and simple design of the instrumentation 10, the navigation system 24 is, in the present case, configured as hand-held, integrated navigation system. It is, for example, a smartphone 44 or a tablet computer. As used herein, "integrated" is, in particular, to be understood as meaning that the components of the navigation system 24 are arranged in a common housing 46 of the navigation system 24. For example, the navigation system 24 has a data processing unit 48 arranged in the housing 46.

Furthermore, an optical detection unit 52 comprising a camera 50 is arranged in the housing 46. Precisely one digital camera 50 is expediently provided. Also arranged in the housing 46 is an indication unit, configured as display unit 54. In particular, the display unit 54 is a touch screen.

Furthermore, the navigation system 24 has an illumination unit 56 arranged in the housing 46 and, in particular, comprising an LED light source. With the illumination unit 56, in particular, visible light can be emitted in the direction of the marking device 22, and light reflected by its marking elements 36 can be received by the camera 50.

The data processing unit 48 comprises, for example, a microprocessor or is configured as such, on which an application program of the navigation system 24 can be executed. The application program includes, in particular, algorithms for the image processing.

The instrumentation 10 may further comprise a storage unit 58 which is preferably arranged in the housing 46 of the navigation system 24. Information about the article 12, for example, its type and, in particular, its dimensions such as length, width, curvature or diameter can be stored in the storage unit 58.

With the instrumentation 10, the shape of the rod 32 can be easily determined using the navigation system 24. For this purpose, the operator can take images of the marking device 22 and the rod 18 with the camera 50, as illustrated schematically in FIG. 1 (without operator).

The data processing unit 48 is programmed to determine the position and, in particular, the shape of the rod 18 on the basis of one image taken by the camera 50. This is, in particular, possible, on the basis of the known spatial arrangement of the marking device 22 relative to the rod 18, owing to location and orientation of the rod 18 also being able to be concluded from location and orientation of the marking device 22 relative to the camera 50, as explained above. The algorithms for the image processing which are filed in the navigation system 24 analyze the image of the camera 50.

Information about the article 12, which is stored in the storage unit 58, can be used in addition to analyze the image. This makes it possible, for example, to identify the article 12 as rod 18 and to thereby determine its shape more easily.

Preferably, it can be indicated to the operator on the display unit 54 that and how, in particular, in which orientation, the at least one image should be taken. It is expedient, in the case of an article 12 having a longitudinal extent, such as the rod 18, for an optical axis of the camera 50 to be aligned approximately transversely to the longitudinal extent of the article 12.

It is also conceivable for the operator to take two or more images of the marking device 22 and the rod 18 preferably in a different orientation with the camera 50. This allows the data processing unit 48 to determine the shape and position of the rod 18 even more reliably. With more than two images, it is advantageous for the images and the respective orientation of the navigation system 24 relative to the marking device 22 and to the rod 18 to differ from one another in pairs.

The images themselves or a representation of the rod 18, determined on the basis of the one or more images, can be shown on the display unit 54. This is shown schematically in FIG. 1.

The instrumentation 10 allows, in particular, the shape and position of the rod 18 to be determined preoperatively, ex situ or advantageously also in situ.

When the shape of the rod 18 is determined, the data processing unit 48 can ascertain whether the rod 18 has the necessary shape and, in particular, curvature, for the bone screws 34 to be able to be connected to one another as intended. If this is the case, the rod 18 can be implanted with the implantation tool 20.

It proves particularly advantageous that the marking device 22 is fixed to the implantation tool 20. By tracking the marking device 22 with the navigation system 24, the rod 18 can be tracked during the implantation. On the display unit 54, the user can be given instructions for guiding the implantation tool 20 as the shape and the position of the rod 18 are known in the reference coordinate system. It is assumed that the position of the bone screws 34 is known in the reference coordinate system defined by the marking device 22. For example, one of the bone screws 34 is provided with a marking device not shown in the drawings and the position of the other bone screws 34 relative to this marking device is known. The rod 18 can thereby be tracked during insertion relative to the bone screws 34.

FIG. 2 shows a reshaping device 26 for changing the shape of the rod 18. The reshaping device 26 is configured as bending device 62, in particular, as hand-held and hand-operated bending pliers. The bending device 62 comprises, for example, branches 64 pivotable relative to each other. Contact elements 68 for positioning on the rod 18 can be arranged at a distal end 66 of the branches 64. The rod 32 can be bent by manual actuation.

A further marking device 28 is preferably arranged on the bending device 62. As with the marking device 22, the marking device 28 can be tracked in a corresponding manner by the navigation system 24 and corresponds in its function thereto.

If the shape of the rod 18 that has been determined on the basis of the one image does not correspond to the necessary shape, the rod 18 can be given the desired shape by bending with the bending device 62. For this purpose, it is, for example, possible for the data processing unit 48 to provide the operator with instructions on the display unit 54 as to how to actuate the bending device 62.

The bending of the rod 18 can take place, in particular, in situ. In doing so, it is advantageous for the bending device 62 to be tracked by the navigation system 24 via the marking device 28. This makes it possible to give the operator instructions, in particular, in situ for bending the rod 18. Attachment points of the contact elements 68 on the rod 18, the bending plane and the bending radius can be checked and verified by tracking the bending device 62 relative to the rod 18. If necessary, the operator can be provided with instructions on the display unit 54 for repositioning the bending device 62 on the rod 18.

Instead of the hand-operated reshaping device 26, a mechanical reshaping device may also be used, as explained above.

Figure 3:
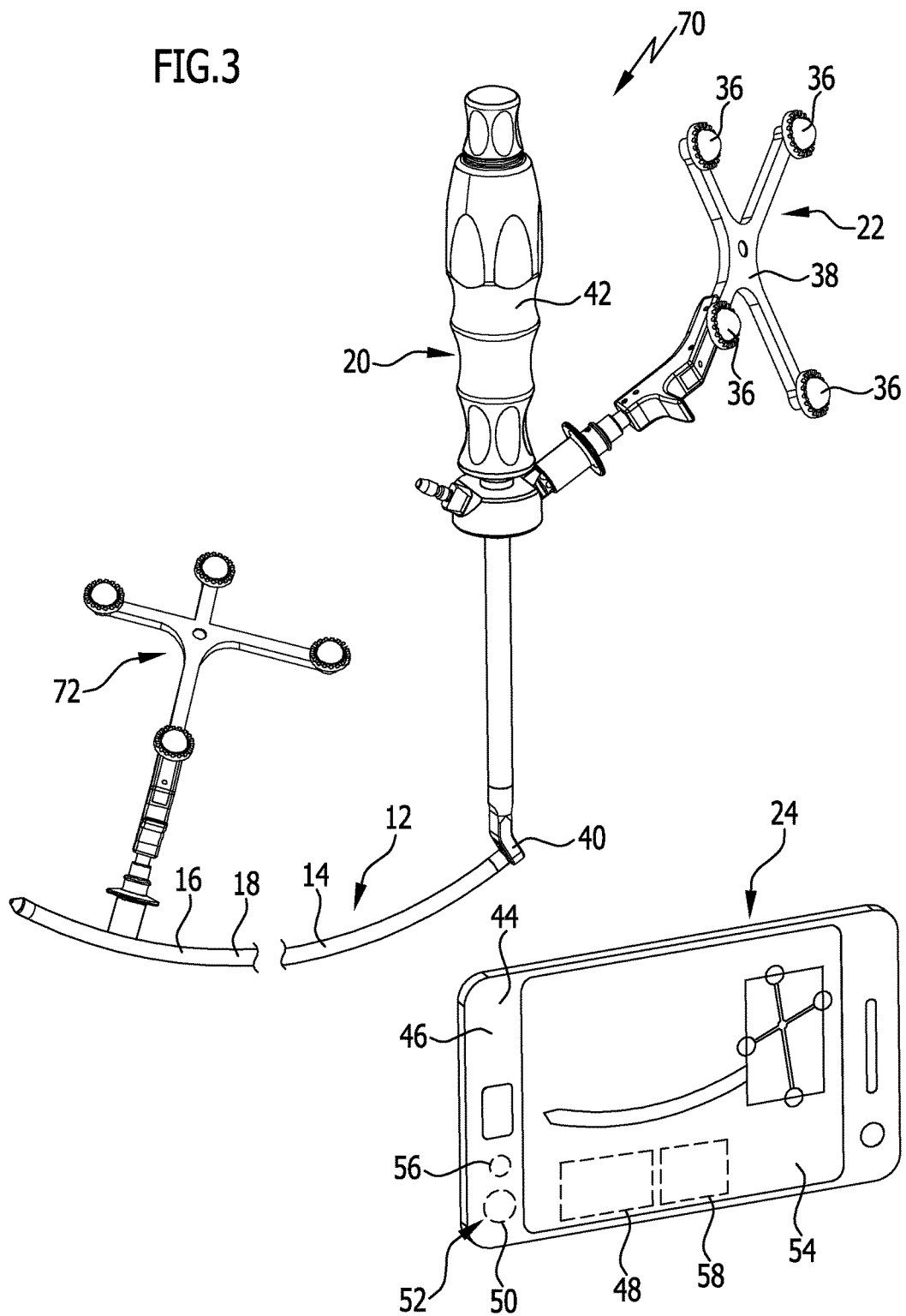
FIG. 3: a schematic perspective partial illustration (with the exception of a reshaping device) of a further embodiment of the instrumentation in accordance with the invention.

FIG. 3 shows in a way similar to FIG. 1 a second advantageous embodiment, denoted by reference numeral 70, of an instrumentation in accordance with the invention.

The advantages achievable with the instrumentation 10 can also be achieved with the instrumentation 70. To avoid repetitions, reference is to be had to statements made hereinabove. The reshaping device 26 may be a component of the instrumentation 70.

The same reference numerals are used for features and component parts of the instrumentations 70 and 10, which are the same or have the same effect.

In the instrumentation 70, the rod 18 is of longer configuration in comparison with the embodiment of the instrumentation 10.

The instrumentation 70 also comprises a further marking device 72 which as with the marking device 22 can be tracked in a corresponding manner by the navigation system 24 and corresponds in its function thereto. The marking device 72 can be releasably fixed, for example, by clamping to the rod 18 at different positions. FIG. 3 shows schematically a fixing of the marking device 72 in the area of a distal end section of the rod 18.

In this way, the marking device 72 is positioned in a defined spatial arrangement in relation to the rod 18.

Several images, which each record at least one marking device 22, 72 and a section of the rod 18 can be taken with the camera 50. For example, a section of the rod 18 with the marking device 72 is recorded. The position and the shape of this section of the rod 18 can be determined on the basis of a respective image by the data processing unit 48.

This makes it possible to record the shape of the rod 18 successively by several images, and a referencing of the position of the rod 18 can be carried out all in all jointly using the marking device 22.

Figure 4:
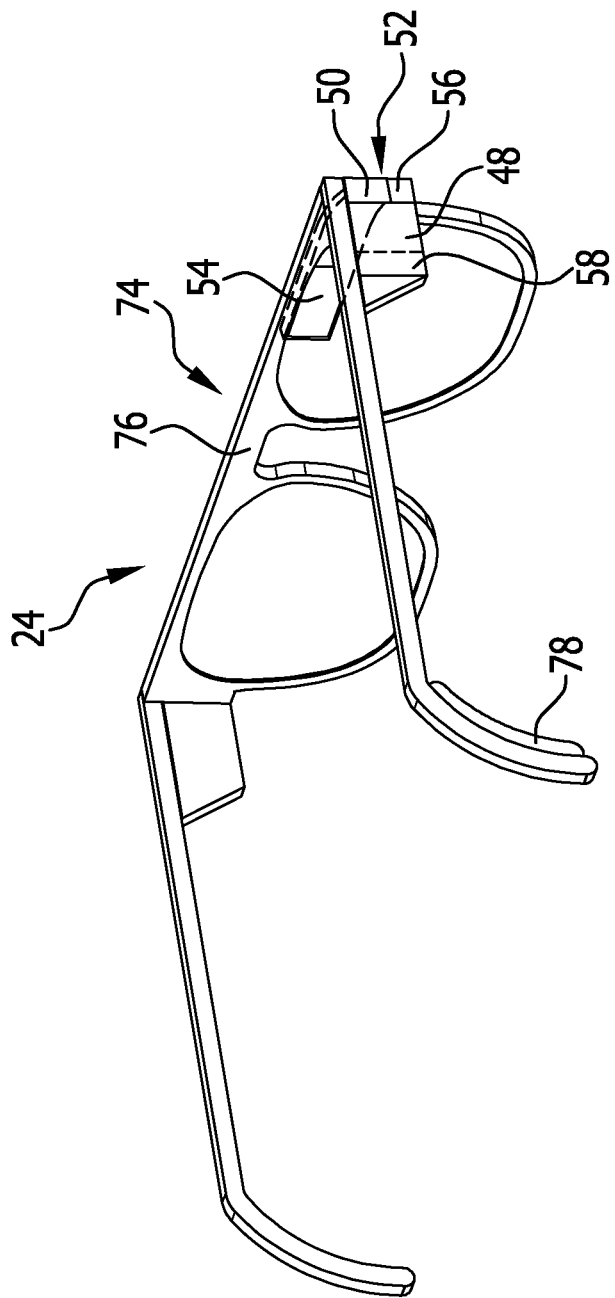
FIG. 4: a schematic perspective illustration of a navigation system of an instrumentation in accordance with the invention.

FIG. 4 shows, in comparison with the smartphone 44, a different configuration of a navigation system 24, namely in the form of smart glasses 74. The smart glasses 74 may be used instead of or in addition to the smartphone 44 in an instrumentation in accordance with the invention, i.e., in particular, the instrumentations 10 and/or 70.

The smart glasses 74 may be worn by an operator not shown in the drawings in the manner of ordinary glasses, resting on the ears and on the nose. It may be provided that lenses are fitted in the glasses frame 76, but this is not absolutely necessary.

The detection unit 52 comprising the camera 50, the data processing unit 48, the storage unit 58 and the display unit 54 are held on the smart glasses. As with the smartphone 44, the operator can in a corresponding manner be shown image contents on the image display of the display unit 54.

The illumination unit 56 is also held on the glasses frame 76. Furthermore, a battery 78 may be held on the glasses frame 76 for supplying energy.

LIST OF REFERENCE NUMERALS 10 instrumentation
12 article
14 implant
16 stabilization element
18 rod
20 implantation tool
22 marking device
24 navigation system
26 reshaping device
28 marking device
30 vertebral bodies
32 anchoring element
34 bone screw
36 marking element
38 holder
40 distal end
42 grip element
44 smartphone
46 housing
48 data processing unit
50 camera
52 detection unit
54 display unit
56 illumination unit
58 storage unit
62 bending device
64 branch
66 distal end
68 contact element
70 instrumentation
72 marking device
74 smart glasses
76 glasses frame
78 battery

What is claimed is:

1. Medical instrumentation comprising:
a navigation system, the navigation system comprising a housing, a display unit, an optical detection unit comprising a camera, and a data processing unit coupled to the detection unit,
a medical article, and
a marking device,
wherein:
the marking device is held directly or indirectly on the article and the marking device is positioned in a defined spatial arrangement in relation to the article; or the article comprises the marking device,
a location and orientation of the marking device is determinable with the navigation system,
a position and three-dimensional shape of the article is determinable by the data processing unit on the basis of a single image of the marking device and the article taken by the optical detection unit,
the data processing unit executes image processing algorithms to analyze the single image, the navigation system is a hand-held, integrated navigation system, the optical detection unit, the data processing unit, and the display unit are disposed in the housing.

2. Instrumentation in accordance with claim 1, wherein information about the article which is used by the data processing unit when determining the shape of the article is stored in a storage unit.

3. Instrumentation in accordance with claim 1, wherein the navigation system is a smartphone or a tablet computer.

4. Instrumentation in accordance with claim 1, wherein the navigation system is or comprises smart glasses.

5. Instrumentation in accordance with claim 1, wherein:
the display unit is coupled to the data processing unit,
the display unit is adapted to show at least one of: the image of the article; instructions for an operator for taking the image; and a representation of the article, determined on the basis of the image.

6. Instrumentation in accordance with claim 1, wherein the article is a surgical instrument, or wherein the article is an implant.

7. Instrumentation in accordance with claim 6, wherein the instrumentation comprises an implantation tool for the implant, on which the implant and the marking device are held.

8. Instrumentation in accordance with claim 6, wherein the implant is a stabilization element of a surgical fixation system.

9. Instrumentation in accordance with claim 8, wherein the stabilization element is a rod.

10. Instrumentation in accordance with claim 8, wherein the instrumentation comprises a reshaping device with which the shape of the stabilization element is changeable.

11. Instrumentation in accordance with claim 10, wherein the reshaping device is a bending device for bending a rod.

12. Instrumentation in accordance with claim 6, wherein the surgical instrument is a screwing instrument or a drive-in instrument.

13. Instrumentation in accordance with claim 1, wherein the article comprises marking elements of the marking device, configured as points or lines on the article.

14. Instrumentation in accordance with claim 1, wherein the marking device is releasably fixed on the article.

15. Instrumentation in accordance with claim 1, wherein the marking device is integrally connected to the article.

16. Instrumentation in accordance with claim 15, wherein a predetermined breaking point is provided for separating the marking device from the article.

17. Instrumentation in accordance with claim 1, wherein:
a plurality of marking devices are held directly or indirectly on the article and the plurality of marking devices are positioned in a defined spatial arrangement in relation to the article, or the article comprises the marking devices, and
the position and shape of a section of the article is determinable by the data processing unit on the basis of several images which each record at least one marking device and the section of the article.

18. Method for determining the shape of a medical article using a medical instrumentation comprising: a navigation system which comprises a housing, a display unit, an optical detection unit comprising a camera, and a data processing unit coupled to the detection unit; a medical article; and a marking device which is held directly or indirectly on the article, the marking device being positioned in a defined spatial arrangement in relation to the article, or the article comprises the marking device, the method comprising:
determining a location and orientation of the marking device with the navigation system, and
determining a position and three-dimensional shape of the article by the data processing unit on the basis of a single image of the marking device and the article taken by the optical detection unit, and
wherein: the data processing unit executes image processing algorithms to analyze the single image, the navigation system is a hand-held, integrated navigation system, the optical detection unit, the data processing unit, and the display unit are disposed in the housing.

* * * * *